(12) United States Patent
Tanaka et al.

(10) Patent No.: US 10,290,099 B2
(45) Date of Patent: May 14, 2019

(54) IMAGE PROCESSING DEVICE AND IMAGE PROCESSING METHOD

(71) Applicant: HITACHI, LTD., Tokyo (JP)

(72) Inventors: Shino Tanaka, Tokyo (JP); Takashi Shirahata, Tokyo (JP); Hiroki Taniguchi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 15/528,673

(22) PCT Filed: Dec. 2, 2015

(86) PCT No.: PCT/JP2015/083851
§ 371 (c)(1),
(2) Date: May 22, 2017

(87) PCT Pub. No.: WO2016/104082
PCT Pub. Date: Jun. 30, 2016

(65) Prior Publication Data
US 2017/0278242 A1 Sep. 28, 2017

(30) Foreign Application Priority Data

Dec. 26, 2014 (JP) ................................ 2014-264739

(51) Int. Cl.
*A61B 5/00* (2006.01)
*G06T 7/00* (2017.01)
(Continued)

(52) U.S. Cl.
CPC ............ *G06T 7/0012* (2013.01); *A61B 5/055* (2013.01); *A61B 6/03* (2013.01); *A61B 6/032* (2013.01);
(Continued)

(58) Field of Classification Search
CPC ................ G06K 9/00; G06T 7/00; A61B 5/00
(Continued)

(56) References Cited

U.S. PATENT DOCUMENTS

2006/0157069 A1* 7/2006 Matsumoto ............ A61B 6/032
128/898
2012/0230559 A1* 9/2012 Itai ........................ G06T 7/0012
382/128

FOREIGN PATENT DOCUMENTS

| JP | 2006-198059 | 8/2006 |
| JP | 2011-135936 | 7/2011 |
| JP | 2012-187161 | 10/2012 |

OTHER PUBLICATIONS

International Search Report dated Mar. 1, 2016 in connection with PCT/JP2015/083851.

\* cited by examiner

*Primary Examiner* — Abolfazl Tabatabai
(74) *Attorney, Agent, or Firm* — Cooper & Dunham LLP

(57) ABSTRACT

There is provided an image processing device capable of generating a more accurate analysis image by extracting a region, which exists at a boundary between different substances and has a pixel value that is non-uniform and continuously changes, from volume data. The image processing device acquires the volume data of a region which includes a large intestine, sets a plurality of starting points of region expansion in a boundary region between air and a residue in the large intestine, sets a condition of an expandable range of a width according to a gradient of a pixel value of each of the starting points, performs a region expansion process from each of the starting points according to the set condition, and generates the analysis image based on the result of the region expansion process.

10 Claims, 17 Drawing Sheets

(51) Int. Cl.
*A61B 6/03* (2006.01)
*A61B 5/055* (2006.01)
*G06T 7/11* (2017.01)
*G06K 9/46* (2006.01)
*A61B 6/00* (2006.01)
*G06T 7/12* (2017.01)

(52) U.S. Cl.
CPC .............. *A61B 6/481* (2013.01); *A61B 6/504* (2013.01); *G06K 9/4604* (2013.01); *G06T 7/11* (2017.01); *G06T 7/12* (2017.01); *G06T 2207/10028* (2013.01); *G06T 2207/10081* (2013.01); *G06T 2207/10088* (2013.01); *G06T 2207/30028* (2013.01); *G06T 2207/30101* (2013.01)

(58) Field of Classification Search
USPC .......................................................... 382/131
See application file for complete search history.

FIG.7
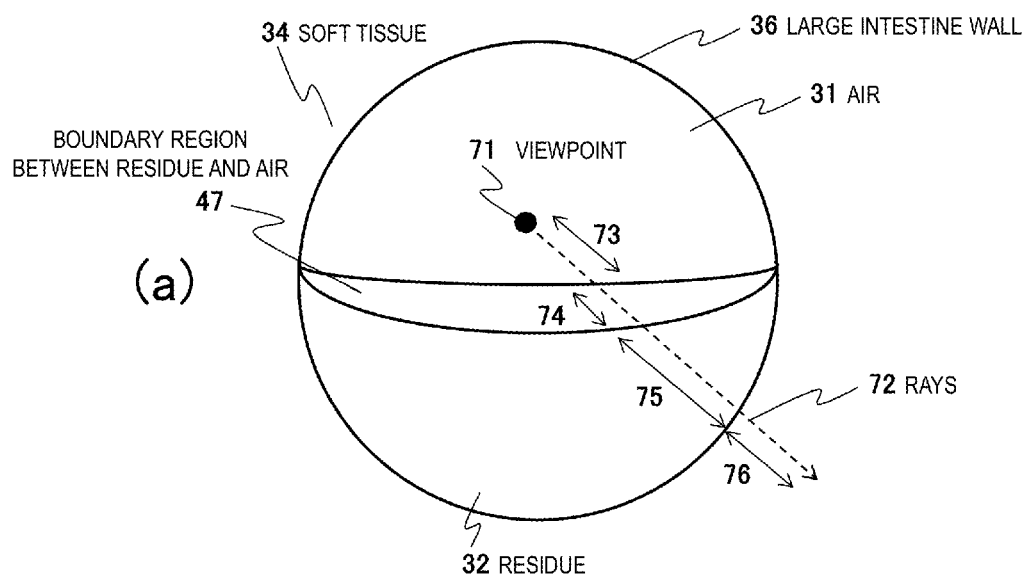
(a)
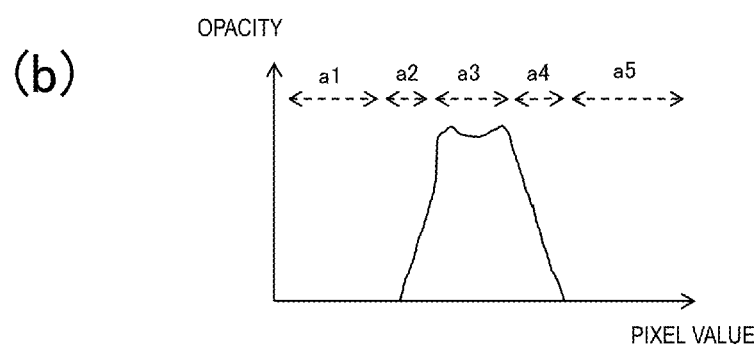
(b)

FIG.9
(a) 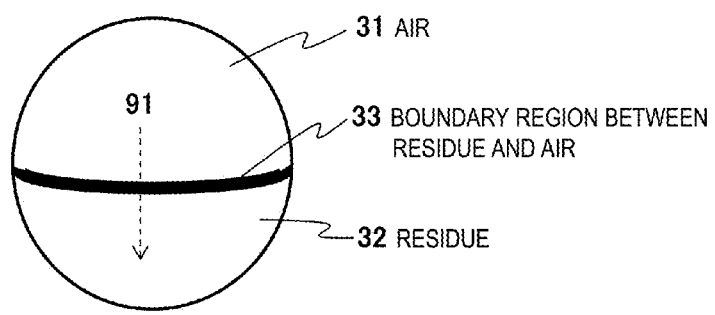
(b) 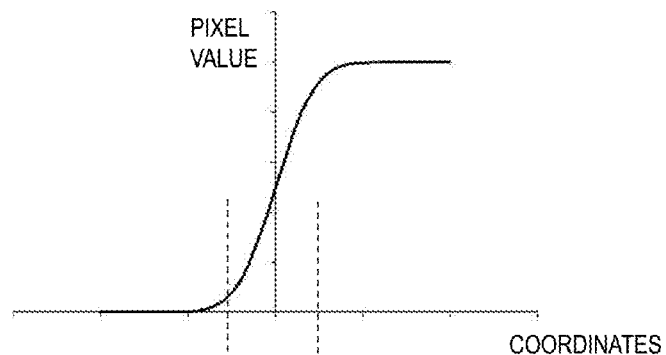
(c) 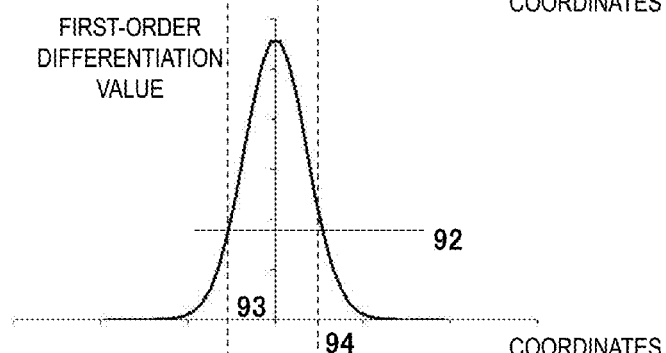
(d) 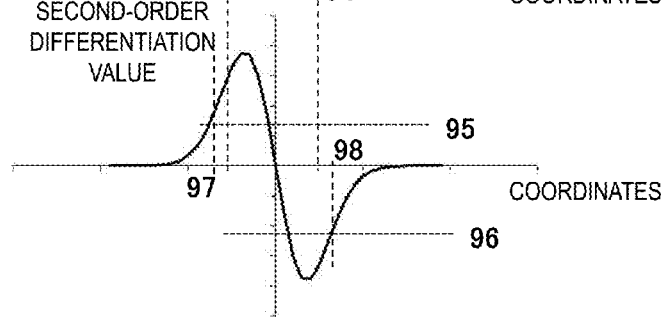

FIG.10
(a)
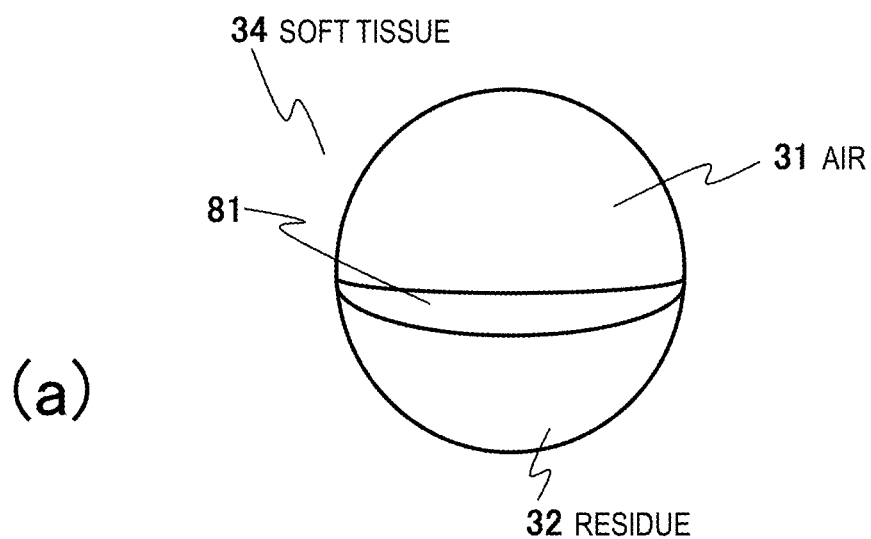
(b)
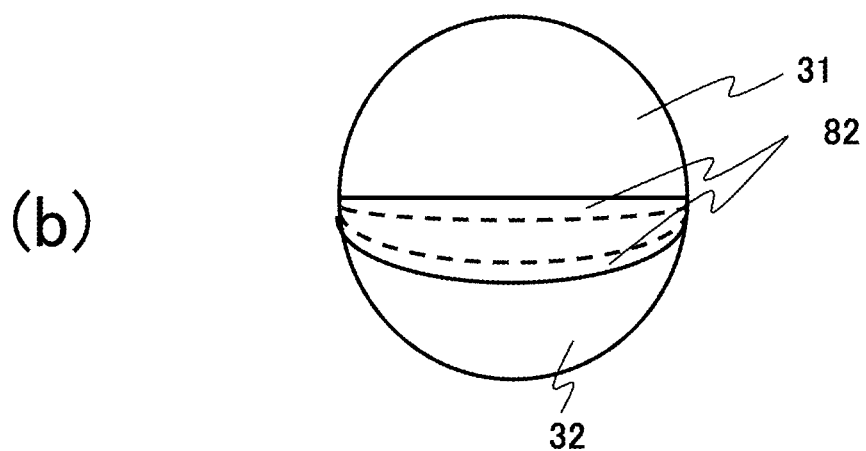

FIG.17
(a)　　　　　　　(b)
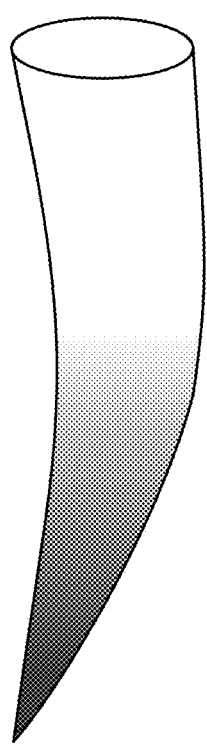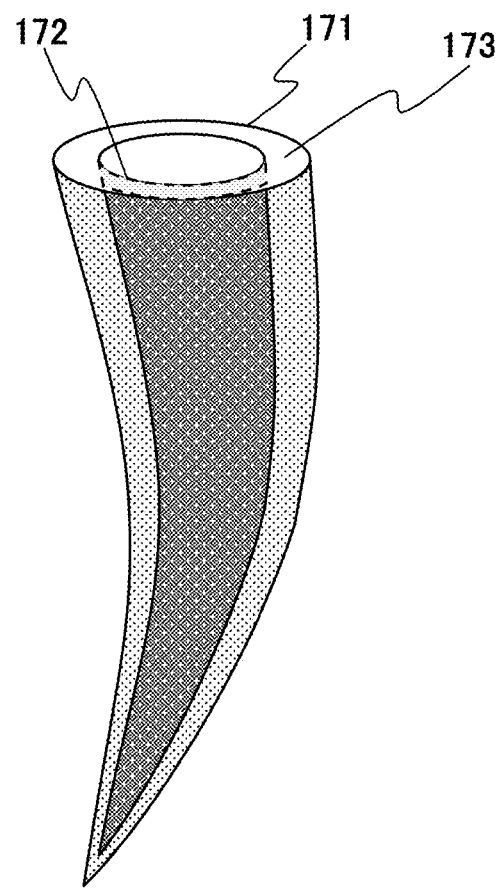

IMAGE PROCESSING DEVICE AND IMAGE PROCESSING METHOD

TECHNICAL FIELD

The present invention relates to an image processing device and an image processing method, and, particularly to, a region expansion process which is used in a case where a prescribed region is extracted from a CT image and an MR image.

BACKGROUND ART

A method of generating a three-dimensional image (three-dimensional volume data) from a tomographic image group, which is scanned by an X-ray Computed Tomography (CT) device and a Magnetic Resonance Imaging (MRI) device, and generating and displaying an image (hereinafter, referred to as an analysis image) which is suitable for diagnosis is known. For example, a three-dimensional volume rendering image, a Maximum Intensity Projection (MIP) image, or the like is generated as the analysis image.

However, in a case where an abdominal region is scanned using the X-ray CT device or the MRI device in such a way that a luminal organ, such as a large intestine, is expanded by carbon dioxide gas or air, cleaning in the luminal organ is generally necessary. However, it is difficult to completely clean the luminal organ and a residue often remains in the organ. In such a case, it is difficult to discriminate the residue from a lesion and it is inconvenient for image diagnosis. Here, a method called "Fecal Tagging" of imaging the residue using an oral contrast agent and distinguishing between the residue and the lesion by causing a pixel value of the residue on the image to be higher than a CT value of the lesion is used. Furthermore, in recent years, a technology (called residue removing or electronic cleansing) is used in which the contrast residue is removed from the analysis image through an image process.

In the simple residue removing, with regard to a contrast residue region, which is identified by a process of processing the pixel value as a threshold or the like, the analysis image is generated by converting the pixel value into a pixel value corresponding to air. However, at a boundary part between a plurality of substances, such as a boundary between air and a contrast residue, the pixel value continuously changes due to partial volume effect. Therefore, in a simple threshold process, it is difficult to identify and remove a boundary region between two regions (two-layered body region), and thus boundary region is drawn in the analysis image. The partial volume effect is a phenomenon in which, in a case where two regions having different pixel values are in contact with each other in a CT image, a pixel value in the boundary region continuously changes such that the pixel value connects the pixel values of the respective regions.

Here, PTL 1 proposes a method of extracting two layers and a whole boundary thereof in a two-layered body region using a fact that a contrast residue is in contact with an air region in the large intestine.

CITATION LIST

Patent Literature

PTL 1: Japanese Patent No. 4146438

SUMMARY OF INVENTION

Technical Problem

However, in the method of removing the residue in PTL 1, a part having a horizontal direction is selected as a boundary surface part among boundary surface candidates of the two-layered body, and thus the method can be applied to only a liquid contrast residue and it is difficult, to apply the method to a boundary region between a solid contrast residue and air. In addition, in a case where an extraction process is performed under the same condition at an end of the boundary line (a pixel or the like which is close to a peripheral soft tissue of a luminal wall) and a central part in a process for extracting the boundary region between the residue and air in the large intestine, there is a possibility that extraction omission and excess extraction occur because there is a part where a difference in pixel values between a pixel of the residue and a pixel of a periphery (soft tissue) is small at the end.

In the case, the analysis image, which is generated based on the images, may be an image in which the peripheral soft tissue is not accurately drawn. In addition, in a case where the whole two-layered body is extracted, there is a problem in that the surface is roughly drawn because a wall surface of the luminal organ is discontinuously drawn in the analysis image, such as a three-dimensional image, which is generated after the extraction.

In addition, in a case where the luminal organ, such as a blood vessel, is scanned by the X-ray CT device, the MRI device, or the like, the blood vessel is contrast-enhanced using a contrast agent. A blood vessel region, in which pixel values become high due to the contrast agent, is drawn by a three-dimensional analysis image, such as a volume rendering image or a curved Multi-Planar Reconstruction (MPR) image, and the three-dimensional analysis image is used for diagnosis and surgical simulation.

In a case where the analysis image is generated, the image processing device needs to identify the blood vessel region from other regions. However, compared to a thick blood vessel at a center of the aorta, the contrast agent is not sufficiently spread at an end part of the blood vessel, and thus there is a case where imaging is not sufficiently performed. In this case, the pixel values sequentially decrease as advancing from the thick part of the blood vessel to the end part, and thus there is a case where the end part is not recognized as the blood vessel.

The present invention is made in consideration of the above problems, and an object of the present invention is to provide an image processing device and an image processing method which are capable of generating more accurate analysis images by performing a region expansion process for accurately extracting a region, which exists at a boundary between different substances and has a pixel value that is non-uniform and continuously changes, from volume data and using information of an expanded region.

Solution to Problem

In order to achieve the above-described object, in the present invention, there is provided an image processing device including: a volume data acquiring unit, that acquires volume data of an image having a region which exists at a boundary between different substances and has a pixel value that is non-uniform and continuously changes; a setting unit that sets a plurality of region expansion starting points in the region, and sets a condition relevant to a gradient of the pixel value for each of the starting points as a region expansion condition; a region expansion processing unit that performs a region expansion process from the starting point according to the condition; and an image generating unit that generates an analysis image from the volume data based on information of an expansion region which is a region expanded through the region expansion process.

In addition, the present invention provides an image processing method causing a computer to perform a process including: a step of acquiring volume data of an image having a region which exists at a boundary between different substances and has a pixel value that is non-uniform and continuously changes; a step of setting a plurality of region expansion starting points in the region, and sets a condition relevant to a gradient of the pixel value for each of the starting points as a region expansion condition; a step of performing a region expansion process from the starting point according to the condition; and a step of generating an analysis image from the volume data based on information of an expansion region which is a region expanded through the region expansion process.

Advantageous Effects of Invention

According to the image processing device and the image processing method of the present invention, it is possible to generate more accurate analysis images by performing a region expansion process for accurately extracting a region, which exists at a boundary between different substances and has a pixel value that is non-uniform and continuously changes, from volume data and using information of an expanded region.

BRIEF DESCRIPTION OF DRAWINGS

FIG. 7 is a diagram illustrating the analysis image generating process (setting of an opacity and a drawing prohibition region).

FIG. 9(a) is a diagram illustrating a direction in which gradient information is acquired, FIG. 9(b) is a graph illustrating distribution of pixel values in a scanning direction of FIG. 9(a), FIG. 9(c) is a graph illustrating first-order differentiation of the graph of FIG. 9(b), and FIG. 9(d) is a graph illustrating second-order differentiation of the graph of FIG. 9(b).

FIG. 10(a) is a diagram illustrating a boundary region 81 extracted using information of the first-order differentiation, and FIG. 10(b) illustrates a boundary region 82 extracted using information of the second-order differentiation.

FIG. 17(a) is a diagram illustrating a blood vessel acquired before the region expansion process is performed, and FIG. 17(b) is a diagram illustrating a blood vessel acquired after the region expansion is performed on the blood vessel surface.

DESCRIPTION OF EMBODIMENTS

Hereinafter, embodiments of the present invention will be described in detail with reference to the accompanying drawings.

[First Embodiment]

First, a configuration of an image processing system 1, to which an image processing device 100 according to the present invention is applied, will be described with reference to FIG. 1.

Figure 1:
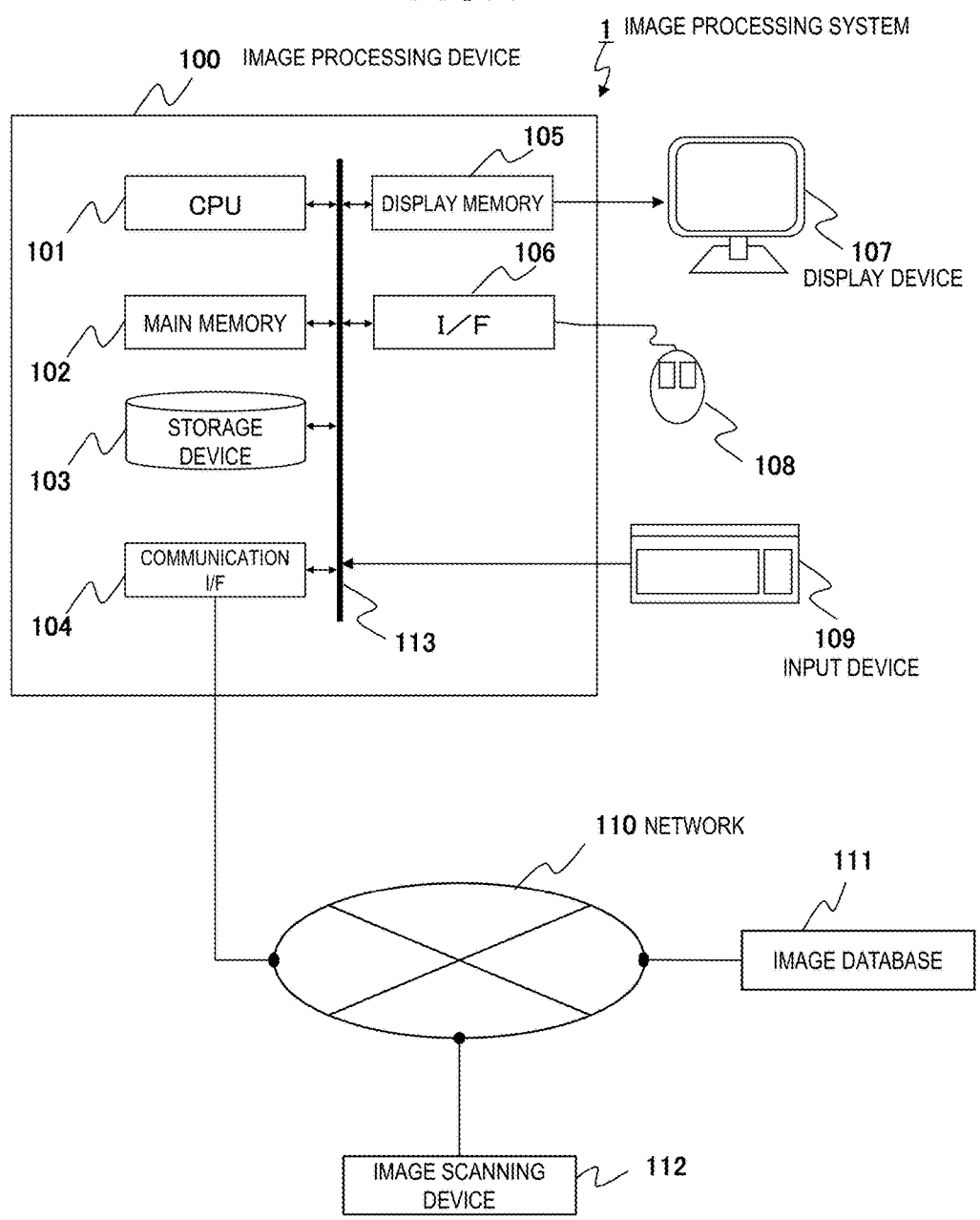
FIG. 1 is a diagram illustrating an entire configuration of an image processing device 100.

As illustrated in FIG. 1, the image processing system 1 includes an image processing device 100, which has a display device 107 and an input device 109, and an image database 111 and an image scanning device 112 which are connected to the image processing device 100 through a network 110.

The image processing device 100 is a computer which performs a process of generating an image, analyzing an image, and the like. For example, the image processing device 100 includes a medical image processing device which is installed in a hospital or the like.

As illustrated in FIG. 1, the image processing device 100 includes a Central Processing Unit (CPU) 101, a main memory 102, a storage device 103, a communication interface (communication I/F) 104, a display memory 105, and an interface (I/F) 106 with an external device such as a mouse 108. The respective units are connected to each other through a bus 113.

The CPU 101 calls a program, which is stored in the main memory 102, the storage device 103, or the like, to a work memory region on a RAM of the main memory 102, executes the program, drives and controls the respective units which are connected through the bus 113, and realizes various processes which are performed by the image processing device 100.

In addition, the CPU 101 performs an analysis image generating process (see FIG. 2) of generating an analysis image, which is used for image diagnosis, based on volume data which is acquired by stacking tomographic images such as CT images. The analysis image generating process will be described in detail later.

The main memory 102 includes a Read Only Memory (ROM), a Random Access Memory (RAM), and the like. The ROM permanently maintains a booting program of a computer, a program such as a BIOS, data, and the like. In addition, the RAM temporarily maintains a program, data, and the like which are loaded from the ROM, the storage device 103, and the like, and includes a work area which is used in a case where the CPU 101 performs various processes.

The storage device 103 is a storage device which reads and writes data from and to a Hard Disk Drive (HDD) and another recording medium, and stores a program, which is executed by the CPU 101, data, which is necessary to execute the program, an Operating System (OS), and the like. With regard to the program, a control program, which corresponds to the OS, and an application program are stored. Codes of the respective programs are read by the CPU 101 if necessary, transferred to the RAM of the main memory 102, and executed as various units.

The communication I/F 104 includes a communication control device, a communication port, and the like, and mediates communication between the image processing device 100 and the network 110. In addition, the communication I/F 104 controls communication with the image database 111, another computer, or the image scanning device 112, such as an X-ray CT device or an MRI device, through the network 110.

The I/F 106 is a port which is used to connect a peripheral device, and transmits and receives data to and from the peripheral device. For example, a pointing device, such as the mouse 108 or a stylus pen, may be connected through the I/F 106.

The display memory 105 is a buffer which temporarily accumulates display data which is input from the CPU 101. The accumulated display data is output to the display device 107 at a prescribed timing.

The display device 107 includes a display device, such as a liquid crystal panel or a CRT monitor, and a logical circuit which performs a display process in association with the display device, and is connected to the CPU 101 through the display memory 105. The display device 107 displays the display data, which is accumulated in the display memory 105, under the control of the CPU 101.

The input device 109 is, for example, an input device such as a keyboard, and outputs various instructions and information, which are input by an operator, to the CPU 101. The operator interactively operates the image processing device 100 using external devices such as the display device 107, the input device 109, and the mouse 108.

The network 110 includes various communication networks, such as a Local Area Network (LAN), a Wide Area Met work (WAN), the Intranet, and the Internet, and mediates communication connection between the image database 111 or a server, another information device, and the image processing device 100.

The image database 111 accumulates and stores image data which is scanned by the image scanning device 112. In the image processing system 1 illustrated in FIG. 1, the image database 111 is configured to be connected to the image processing device 100 through the network 110. However, the image database 111 may be provided in, for example, the storage device 103 in the image processing device 100.

Subsequently, an operation of the image processing device 100 will be described with reference to FIGS. 2 to 7.

Figure 2:
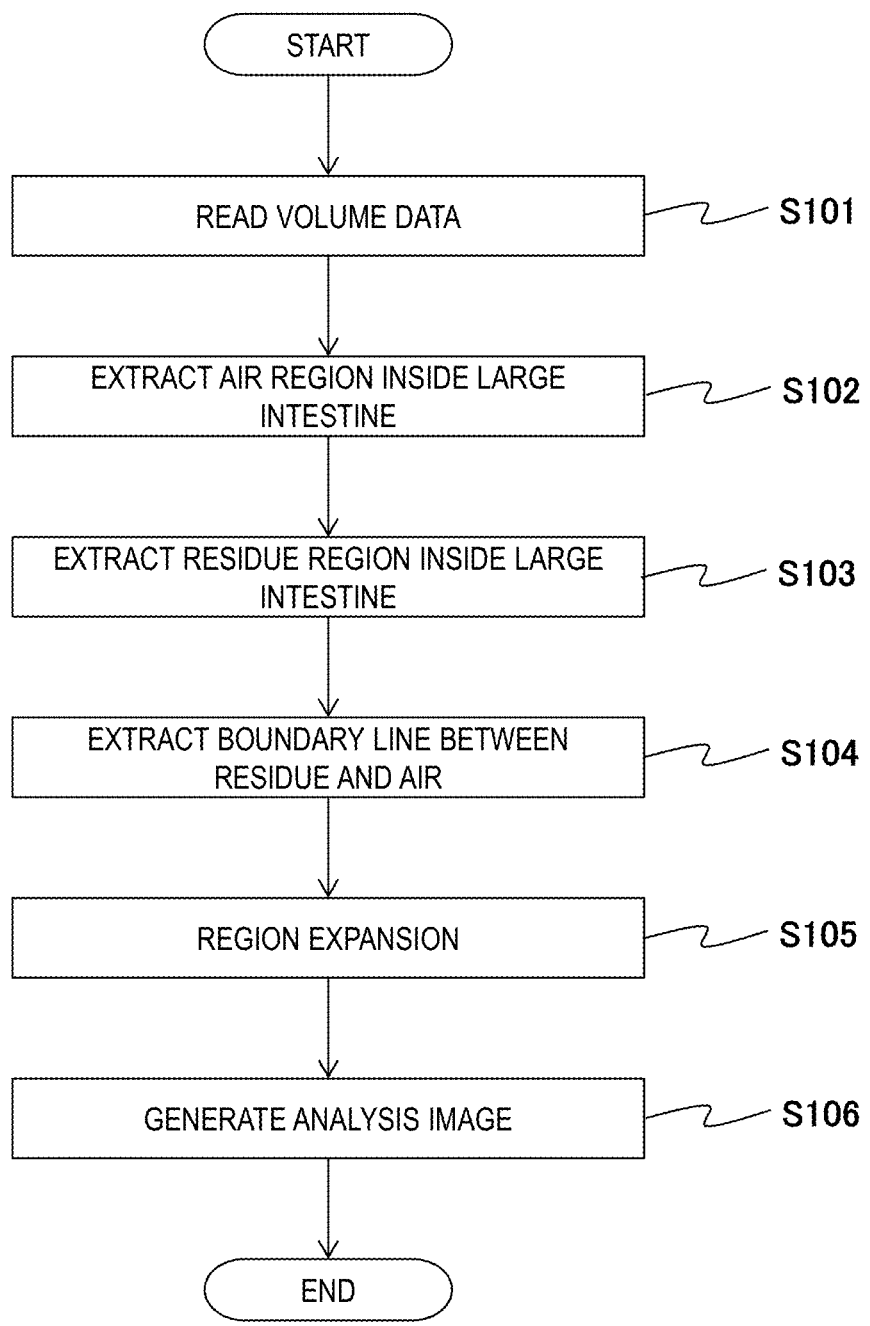
FIG. 2 is a flowchart illustrating a flow of an analysis image generating process performed by the image processing device 100 according to the present invention (first embodiment).

The CPU 101 of the image processing device 100 reads a program and data which are relevant to the analysis image generating process illustrated in FIG. 2 from the main memory 102, and performs the process based on the program and the data.

Meanwhile, in a case where execution of the analysis image generating process starts, it is assumed that image data which is a processing target is fetched from the image database 111 or the like through the network 110 and the communication I/F 104, and is stored in the storage device 103 of the image processing device 100. In addition, it is assumed that the image data which is the processing target is volume data (three-dimensional image) which is acquired by stacking a plurality of tomographic images including a target region. In addition, a CT image, an MR image, or the like maybe a preferable example of the volume data. In the embodiment, with regard to the volume data which is the processing target, the CT image which is acquired by scanning a large intestine region which is expanded by air or the like will be described. Meanwhile, a range to which the present invention is applied is not limited to the large intestine region. For example, it is possible to apply the present invention to a blood vessel region, other luminal organs, and an image which has a boundary region between a plurality of regions having different pixel values.

Figure 3:
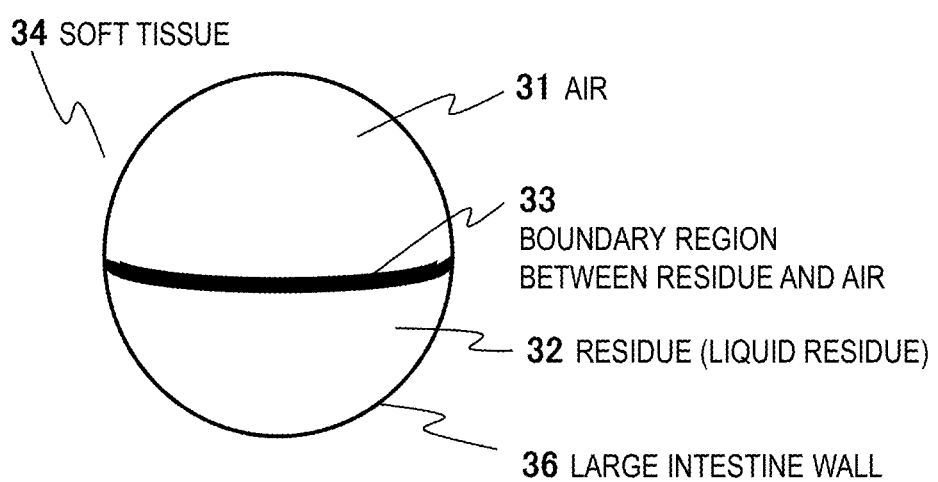
FIG. 3 is a sectional diagram illustrating a large intestine region which includes a residue (liquid residue) 32.

FIG. 3 is a schematic diagram illustrating the inside of the large intestine which includes a contrast residue, and illustrates a section which is approximately perpendicular to a central line of a luminal organ. As illustrated in FIG. 3, the inside of the large intestine includes a boundary region (or a boundary region) 33, which has a finite thickness between an air region 31 and a residue (a residue region or a liquid residue) 32, between the residue and air. A periphery of the large intestine wall 36 is in contact with a soft tissue 34 or the like. In the boundary region 33 between the residue and air, a pixel value is non-uniform, and, in addition, the pixel value continuously changes due to partial volume effect. Therefore, it is difficult to distinguish between the boundary region 33 and the soft tissue 34 through a simple threshold process, and thus it is difficult to extract the boundary region 33. Therefore, in the first embodiment according to the present invention, a region expansion process for extracting the boundary region 33 of a plurality of regions will be described.

Figure 4:
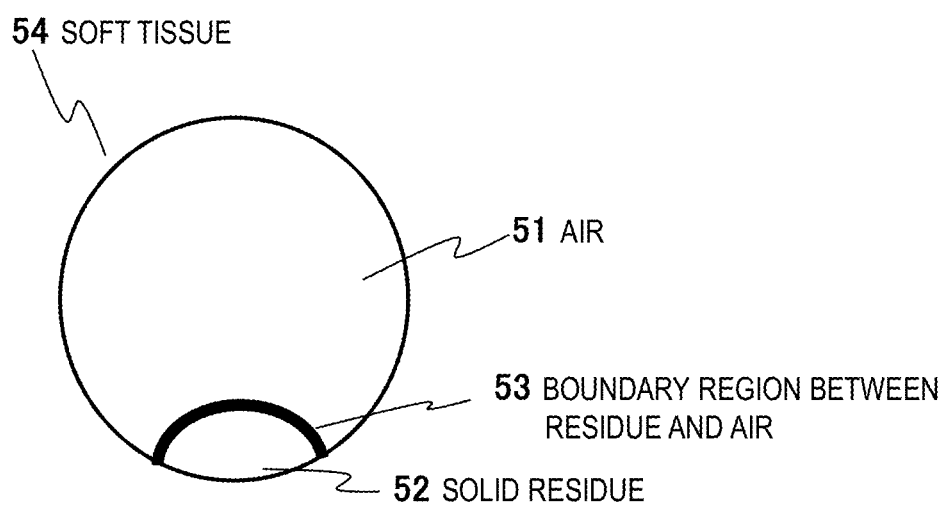
FIG. 4 is a sectional diagram illustrating a large intestine region which includes a solid residue 52.

Meanwhile, although FIG. 3 is a sectional diagram illustrating the large intestine which includes the liquid residue 32, it is possible to apply the present invention to a case where a solid residue 52 as illustrated in FIG. 4 is included.

As illustrated in a flowchart of FIG. 2, first, the CPU 101 reads medical image data which includes the large intestine that is an observation target or a diagnosis target (step S101). The read medical image data is, for example, three-dimensional volume data which is acquired by stacking the tomographic images scanned by a medical image scanning device such as an X-ray CT device. The CPU 101 of the image processing device 100 reads medical image volume data selected by the operator from the storage device 103, and maintains the volume data in the main memory 102.

Subsequently, the CPU 101 analyzes the volume data which is read in step S101, and extracts the air region 31 inside the large intestine using pixel value information, anatomical information, or the like (step S102). In a case where the air-region 31 is extracted, the CPU 101 first extracts an air region outside the living body and a lung field region from the volume data based on, for example, the pixel value information, and recognizes an air region, in which a volume is equal to or larger than a prescribed threshold, as the air region 31 in the large intestine among air regions which are extracted other than the extracted regions.

Subsequently, the CPU 101 analyzes the volume data which is read in step S101, and extracts a residue region 32 inside the large intestine based on the pixel value information or the like (step S103). The CPU 101 extracts a bone region from, for example, the volume data which is read in step S101, and extracts a region, which corresponds to a pixel value of the residue and in which the volume is equal to or larger than the threshold, as the residue region 32 in a part other than the bone region. In addition, the residue region 32 may be extracted using a fact that the residue region 32 is usually positioned on a lower side of the large intestine in a vertical direction. That is, the CPU 101 searches for the lower side of the air region 31, which is extracted in step S102, in the large intestine in the vertical direction, and searches for a pixel corresponding to the residue 32. In a case where the pixel corresponding to the residue 32 is found on the lower side of a few pixels of the air region 31, the residue region 32 is extracted by performing region expansion using the pixel as a starting point.

Subsequently, the CPU 101 extracts a central line (a boundary line between the residue and air) 41 of the boundary region 33 between the residue and air (step S104). In the process for extracting the boundary line 41, for example, the CPU 101 sets scanning lines in the vertical direction over the boundary between the residue region 32 and the air region 31, which are illustrated in FIG. 3, on the tomographic images of the volume data which is read in step S101, acquires gradient information of a pixel value on each of the scanning lines, and sets a starting point of region extraction based on the gradient information. For example, a pixel which has the largest gradient value is extracted for each of the scanning lines, a group of pixels which are extracted on the respective scanning lines is set to the boundary line 41 between the residue and air (FIG. 5), and a plurality of starting points are set on the boundary line 41.

A method of finding the above-described boundary region 33 between the residue and air is realized by, for example, performing raster scanning on the tomographic image in the vertical direction and searching for a boundary pixel P1 on the lower side of the air region 31. Furthermore, the method includes performing the raster scanning from the boundary pixel P1 in the vertical direction and searching for a boundary pixel P2 on an upper side of the residue region 32 in a finite range. In a case where both the boundary pixels P1 and P2 are found, pixels on a line which connects from P1 to P2 are recognized as the boundary region 33 between the residue and air.

The CPU 101 performs the region expansion using the plurality of pixels on the boundary line 41, which is detected in step S104, between the residue and air as the starting points (step S105). Here, an expandable range is individually set for each of the pixels which form the boundary line 41. The expandable range is a finite range in which the CPU 101 performs the region expansion process. For example, the gradient information, positional information, and the like of the pixel of each of the starting points are used to set the expandable range. It is assumed that, in a case where the CPU 101 performs the region expansion process from each of the pixels on the boundary line 41, it is difficult to perform expansion on an outer side than the set expandable range.

The largest value of a distance between the extracted pixel and the pixel of the starting point, the largest value of an expandable generation, and the like may be set using the gradient information, the positional information, and the like of the pixel of each of the starting points which are parameters used to set the expandable range.

Figure 5:
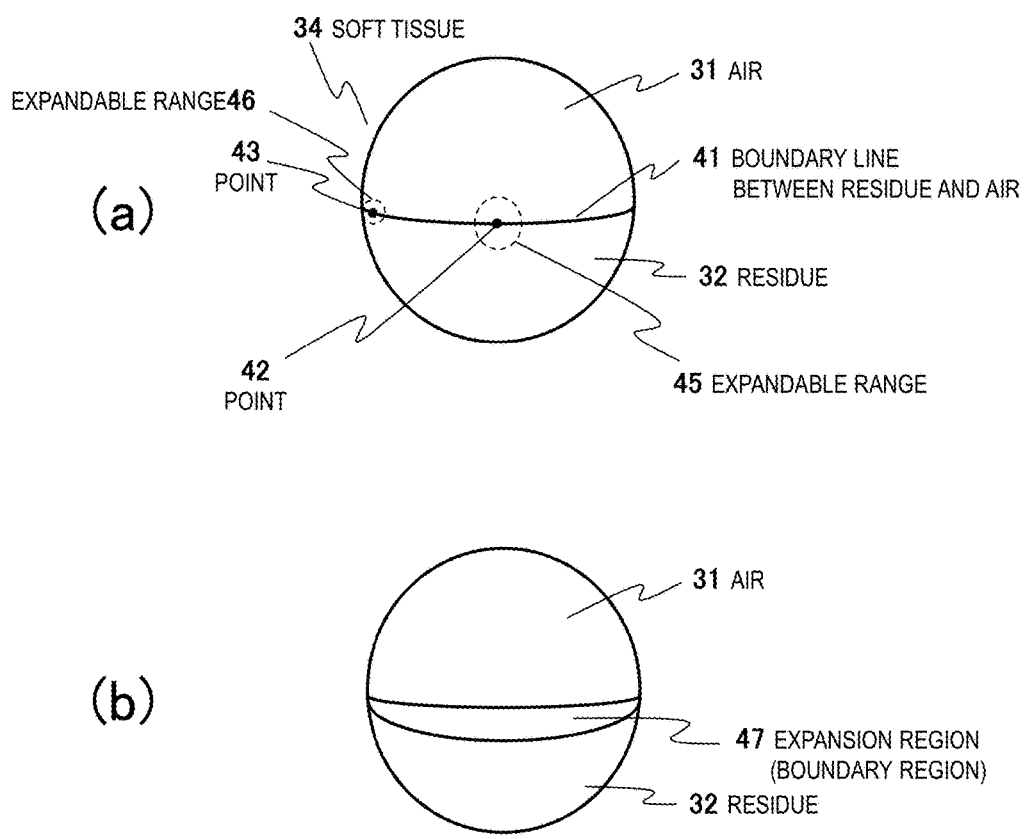
FIG. 5(a) is a diagram illustrating an expansion condition which is set in a region expansion process performed on a boundary part between the liquid residue and air.
FIG. 5(b) is a diagram illustrating an extracted boundary region 47.

An example in which the gradient information is used to set the expandable range will be described with reference to FIG. 5.

In a case where a gradient of a pixel of a point 42 at a central part on the boundary line 41 is compared with a gradient of a pixel of a point 43 which is close to an end, the pixel of the point 43 which is close to the end is close to three regions, that is, the soft tissue 34 (outside region of the large intestine wall), air 31, and the residue region 32. Therefore, it is conceivable that the gradient of the point 43 at the end is smaller than the gradient of the point 42 at the central part. However, since a difference in the pixel values of the soft tissue 34 and the boundary region 33 (FIG. 3) is small, it is difficult to divide the two regions in the region expansion process.

Here, the CPU 101 sets a range (expandable range) in which the expansion region is performed based on the gradient values. For example, the CPU 101 sets a large expandable range in a pixel, which has a large gradient, as in the point 42 at the central part on the boundary line 41 or the like. In contrast, the CPU 101 sets a small expandable range in a pixel which has a small gradient as in the point 43 at the end on the boundary line 41 or the like. Circles 45 and 46, which are illustrated using broken lines in FIG. 5(*a*), respectively indicate the expandable ranges of the points 42 and 43. A large expandable range is set for the point 42 at the central part on the boundary line 41, and a small expandable range is set for the point which is close to the end.

As described above, the CPU 101 sets an expandable range of a width according to the gradient, of the pixel value as a region expansion condition, and performs the region expansion according to the set condition. If so, a crescent-shaped region, such as a region 47 of FIG. 5 (*b*), is extracted. Meanwhile, in the region expansion process, an expansion condition of the pixel value is set as the region expansion condition in addition to the expandable range.

Figure 6:
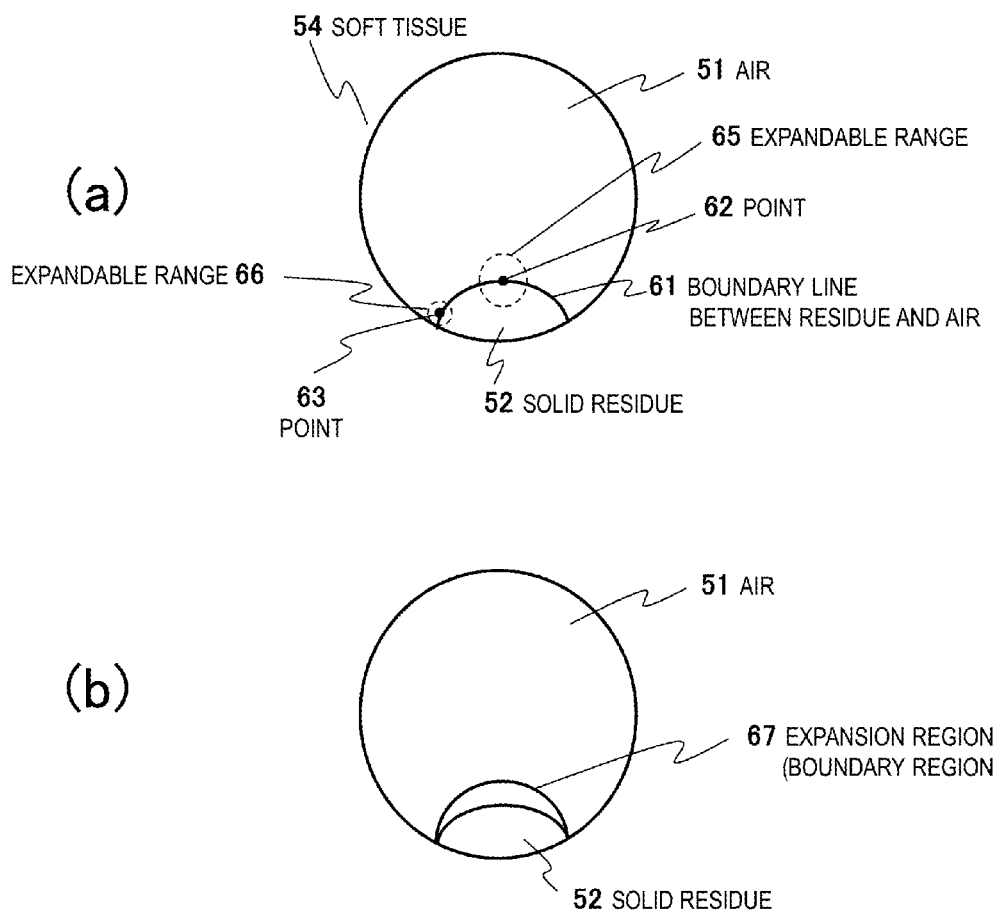
FIG. 6(a) is a diagram illustrating the expansion condition which is set in the region expansion process performed on a boundary part between the solid residue and air.
FIG. 6(b) is a diagram illustrating an extracted boundary region 67.

Meanwhile, although the above description is performed using an example of the liquid residue 32, it is possible to perform the same region expansion process even in a case where the solid residue 52 is included. FIG. 6 is a diagram illustrating the region expansion process in a case where the solid residue 52 is included.

As illustrated in FIG. 6, since a pixel 62 at a central part of a boundary line 61 between air 51 and the solid residue 52 has a large gradient value, the CPU 101 sets a large expandable range (a circle 65 of a broken line which surrounds a point 62). In contrast, the CPU 101 sets a small expandable range at a point 63 at an end of the boundary line 61 (a circle 66 of a broken line which surrounds a point 63). In a case where the region expansion process is performed under the condition (expandable range) which is set as described above, a crescent-shaped region 67 is extracted as illustrated in FIG. 6(*b*).

Returning to the description of FIG. 2. The CPU 101 generates the analysis image based on information of the boundary regions 47 and 67 between the residue and air which are extracted in step S105 (step S106). In the description below, a method of generating a virtual endoscopy image as an example of the analysis image will be described. However, the present invention is not limited to the virtual endoscopy image, and it is possible to apply the present invention to a case where a deployed image and another analysis image are generated.

FIG. 7 is a diagram illustrating the virtual endoscopy image which is the analysis image.

As illustrated in FIG. 7, it is considered that rays are scattered in a direction from a viewpoint 71 inside the large intestine toward of a broken-line arrow 72, and color information of a point, through which rays pass, is projected on a certain pixel in a projection image. Here, the CPU 101 sets an opacity for the pixel value (see FIG. 7(b)). The CPU 101 acquires the opacity according the pixel value of the pixel through which rays pass, and adds a value acquired by multiplying color information of the pixel by a parameter such as the opacity.

For example, a case where rays pass through the air region 73 corresponds to an opacity a1. A case where rays pass through the boundary region 74 between the residue and air corresponds to opacities a2, a3, and a4. A case where rays pass through the residue region 75 corresponds to an opacity a5. A case where rays pass through the soft tissue 34 from the large intestine wall 36 corresponds to opacities a4, a3, and a2, respectively. An object is drawn as a value of the opacity becomes large. Therefore, the boundary region 47 between the residue and air and the boundary region between the large intestine wall 36 and the soft tissue 34 are drawn in the generated analysis image (virtual endoscopy image).

Here, in the embodiment, the boundary region 47 between the residue and air, which is extracted in step S105, is set as a drawing prohibition region. If so, a pixel having a pixel value included in the drawing prohibition region is not drawn in the analysis image. In addition, here, it is preferable that an opacity of the air region and an opacity of the residue region are set to "0" and an opacity corresponding to a pixel value between a pixel value of air and the pixel value of the residue continuously changes. In a case where setting is performed as described above, the boundary region between the residue and air is not drawn and the boundary region on a surface of the large intestine wall is smoothly drawn.

The CPU 101 stores the analysis image, which is generated in step S106, in the storage device 103, displays the analysis image or the display device 107, and ends a series of analysis image generating process.

As described above, in the image processing device 100 according to the present invention, the CPU 101 acquires the volume data of the large intestine region, sets a starting point of the region expansion in the boundary region between air and the residue inside the large intestine, sets a condition of the expandable range according to the gradient information of the pixel for each of the pixels in the boundary region, and performs the region expansion process from each of the starting points according to the set condition. Therefore, it is possible to accurately extract a region (boundary region) which has the pixel value that is non-uniform and continuously changes. The CPU 101 generates the analysis image based on the information of the boundary region acquired as described above.

Therefore, it is possible to accurately extract the boundary region which has the pixel value that is non-uniform and continuously changes, between air and the residue from the volume data using the partial volume effect. In addition, it is possible to extract the boundary region without omission even in a region, such as the end (a part which is close to the large intestine wall) of the boundary line where the difference in the pixel values between the region and the periphery is small.

In a case where the analysis image is generated using regional information recognized as described above, it is possible to draw a surface of the soft tissue which is in contact with the residue without unnecessarily removing the surface, and thus the surface is smoothly drawn without being discontinuous. In addition, a smoothing process is not performed, and thus a small projection is not collapsed. Therefore, in a case where a small lesion candidate exists at a boundary part, it is possible to perform drawing without removing the lesion candidate. In addition, it is possible to apply the method to not only the liquid residue but also the solid residue.

[Second Embodiment]

Subsequently, a second embodiment of the present invention will be described with reference to FIGS. 8 to 10.

In a case where the method according to the first embodiment is used, there is a case where a part of the boundary region remains.

Here, in the second embodiment, a method of extracting the boundary region between the residue and air without omission will be described.

Meanwhile, since a hardware configuration of an image processing device 100 according to the second embodiment is the same as in the first embodiment, the description thereof is not repeated, and the description will be performed by attaching the same reference symbols to the same respective units.

Figure 8:
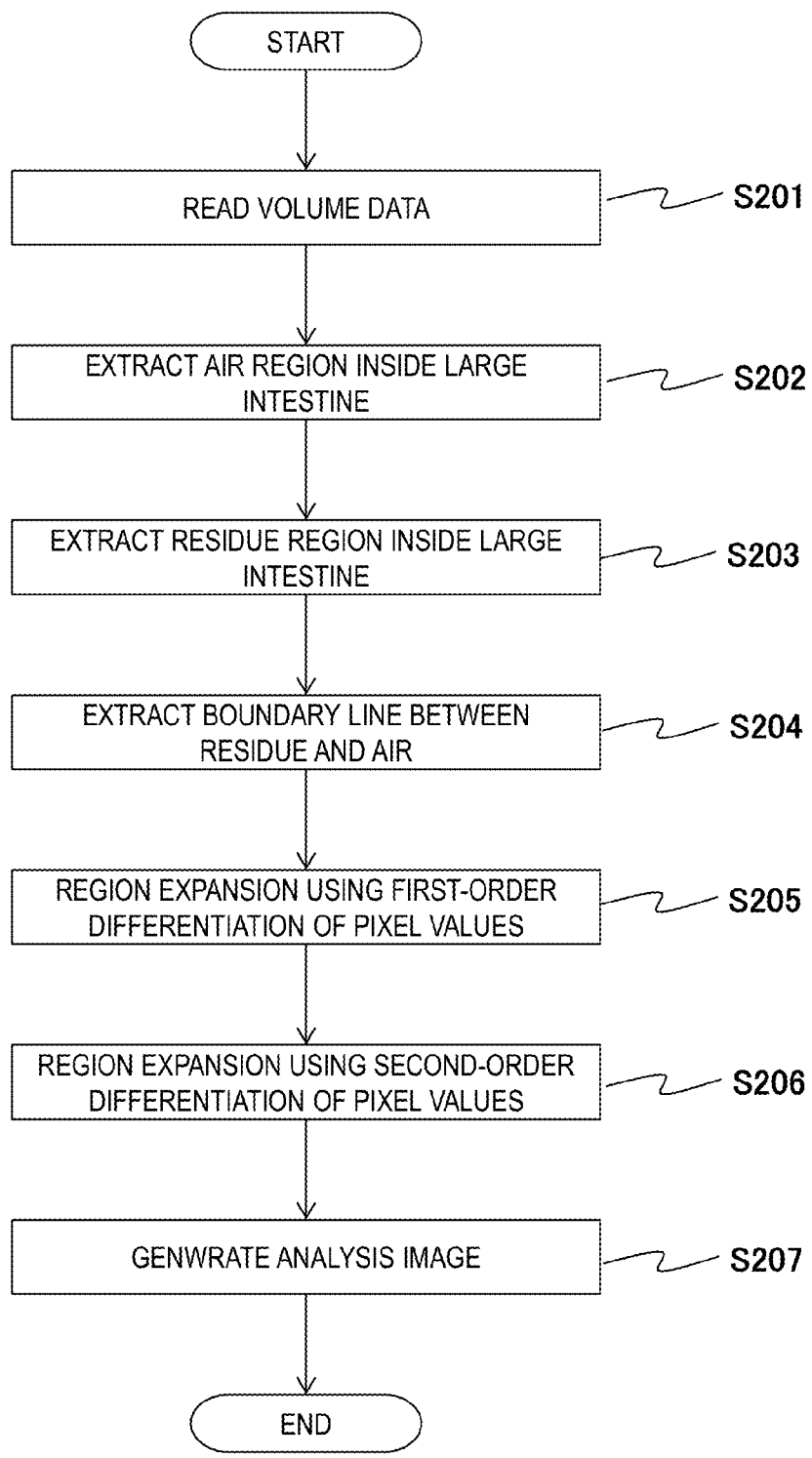
FIG. 8 is a flowchart illustrating the flow of the analysis image generating process performed by the image processing device 100 according to the present invention (second embodiment).

FIG. 8 is a flowchart illustrating a flow of an analysis image generating process according to the second embodiment.

Processes in steps S201 to S204 in FIG. 8 are the same as the processes in steps S101 to S104 of the analysis image generating process (FIG. 2) according to the first embodiment.

That is, the CPU 101 reads medical image data (volume data) which includes a large intestine that is an observation target or a diagnosis target (step S201), analyzes the volume data read in step S201, and extracts the air region 31 inside the large intestine using the pixel value information, the anatomical information, or the like (step S202). In addition, the CPU 101 extracts the residue region 32 inside the large intestine based on the pixel value information or the like (step S203).

Subsequently, the CPU 101 acquires the central line (boundary line) 41 of the boundary region 33 between the residue and air (step S204, see FIG. 5(a)). A method of calculating the central line 41 of the boundary region may be the same as in the first embodiment.

In a case where the air region 31 and the residue region 32 inside the large intestine, and the boundary line 41 between the residue and air are respectively extracted through the processes in steps S202 to S204, the CPU 101 subsequently performs the region expansion process using a first-order differentiation of the pixel value (step S205), and then performs the region expansion process further using a second-order differentiation of the pixel value (step S206).

FIG. 9 is a diagram illustrating the region expansion process in steps S205 and S206. FIG. 9 (b) illustrates a change in the pixel value acquired in a case where the raster scanning is performed on a sectional image of the large intestine illustrated in FIG. 9(a) in a direction of a broken line 91. As illustrated in FIG. 9(b), a smooth change is viewed from a pixel value corresponding to air to the pixel value corresponding to the residue. Furthermore, FIG. 9(c) illustrates a result of the first-order differentiation performed on a graph of FIG. 9(b), and FIG. 9(d) illustrates a result of the second-order differentiation performed on the graph of FIG. 9(b).

In step S205, in a case where a region is expanded from the starting point on the boundary line 41, which is extracted in step S204, between the residue and air, the region expansion process is performed under an expansion condition according to the gradient information. Here, as in the process in step S104 (FIG. 2) according to the first embodiment, the expandable range may be restricted for each of the pixels according to the gradient information. In addition, the expansion condition may be set such that a region is expanded for a pixel in which a size of the gradient of each pixel is equal to or larger than a threshold 92 of FIG. 9(c).

In a case where the expansion condition is set, a range from coordinates 93 to coordinates 94 is extracted as the boundary region between the residue and air.

In addition, a pixel, in which an inner product of a gradient (first-order differentiation), in a case where the region expansion is performed, between a parent pixel and a pixel of interest is equal to or larger than the threshold may be the expansion region.

A value, which is input by a user, or a value, which is acquired in such a way that the medical image processing device 100 analyzes the volume data, may be used as the threshold 92. As a method of setting the threshold 92 by the medical image processing device 100, there is a method in which, for example, the CPU 101 acquires an average value of gradients for the respective pixel values in a range in which the expansion process is performed on the air region and the residue region and sets a pixel value, which is a peak of an average gradient value for the pixel values, as the threshold 92.

In the region expansion process in step S206, a region is further expanded using information of the second-order differentiation based on the region which is extracted in step S205. In the region expansion condition using the information of the second-order differentiation, the region expansion is performed in a case where, for example, a size of the second-order differentiation of the pixel is equal to or larger than a threshold 95 or equal to or smaller than a threshold 96. In a case where the region expansion is performed under the condition, a range from coordinates 97 to coordinates 98 is further expanded.

In a case where the region expansion is performed using the information of the second-order differentiation, it is possible to distinguish and extract only a pixel at a non-uniform part without extracting a pixel at a uniform part even through the pixel values are the same. Therefore, it is preferable to extract a boundary region which has the pixel value that is non-uniform.

Meanwhile, similarly to the method of setting the threshold 92 of the first-order differentiation, in a method of setting the thresholds 95 and 96 of the second-order differentiation, a value which is input by the user may be used and a value which is acquired by analyzing the volume data by the medical image processing device 100 may be used. In addition, the second-order differentiation in a direction along, for example, the gradient acquired through the first-order differentiation may be used as a value of the second-order differentiation in the expansion condition. In addition, the inner product with the second-order differentiation of the parent pixel may be used.

FIG. 10(a) illustrates a boundary region 81 which is extracted in the region expansion process using information of the first-order differentiation in step S205, and FIG. 10(b) illustrates a boundary region to which the region 82, which is extracted in the region expansion process further using the information of the second-order differentiation in step S206, is added.

The CPU 101 generates the analysis image based on information of the boundary region between the residue and air which is extracted in the region expansion process in steps S205 and S206 (step S207). A method of generating the analysis image is the same as in the first embodiment.

As described above, according to the second embodiment, the region expansion process is performed using the information of the first-order differentiation on the scanning lines as the expansion condition of the region expansion condition, and the region expansion is further performed using the information of the second-order differentiation on the above-described scanning line as the expansion condition. Therefore, in a case where the boundary region is expanded, it is possible to extract a non-uniform part without extracting a peripheral part where a pixel value is uniform even in a case of the same pixel value.

Meanwhile, although an example is described in which the boundary region between the contrast residue and air of the luminal organ is extracted in the first and second embodiments, the present invention is not limited thereto. It is possible to apply the present invention to a case where a boundary part between a plurality of regions which have pixel values that are non-uniform and continuously change is extracted from an image.

For example, it is possible to apply the present invention to a case where a contrast blood vessel region which includes a part where the contrast is not sufficient is drawn.

[Third Embodiment]

Subsequently, a third embodiment according to the present invention will be described with reference to FIGS. 11 to 17.

In the third embodiment, an example, in which the region expansion process according to the present invention is applied in a case where the contrast blood vessel region having the part where the contrast is not sufficient is drawn, will be described.

Meanwhile, since a hardware configuration of an image processing device 100 according to the third embodiment is the same as in the first embodiment, the description thereof is not repeated, and the description will be performed by attaching the same reference symbols to the same respective units.

Figure 11:
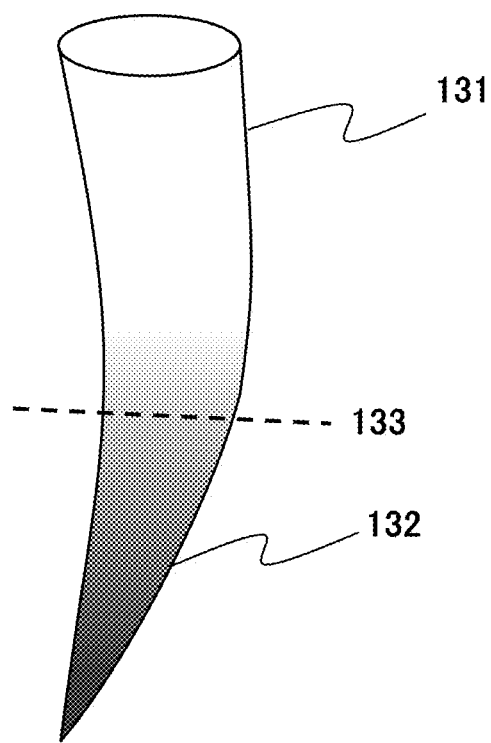
FIG. 11 is a schematic diagram illustrating a blood vessel which has an end part where the contrast is not sufficient.

FIG. 11 is a schematic diagram illustrating a contrast blood vessel which is a processing target in the third embodiment. An end part 132 of the contrast blood vessel is not sufficiently contrast-enhanced. In a case where the region extraction is performed in the blood vessel and the region expansion is performed according to a condition of a thick part 131 of the blood vessel where the contrast is not sufficient, a problem occurs in that extraction is performed only in the middle of (for example, a position of a broken line 133) of the blood vessel. Here, in the third embodiment, a method of drawing up to the end 132 where the contrast is not sufficient is proposed in such a way that the region expansion process is performed on the boundary surface between the inside and the outside of the contrast blood vessel and a range, in which the region expansion is performed, is gradually expanded in a traveling direction of the blood vessel.

Figure 12:
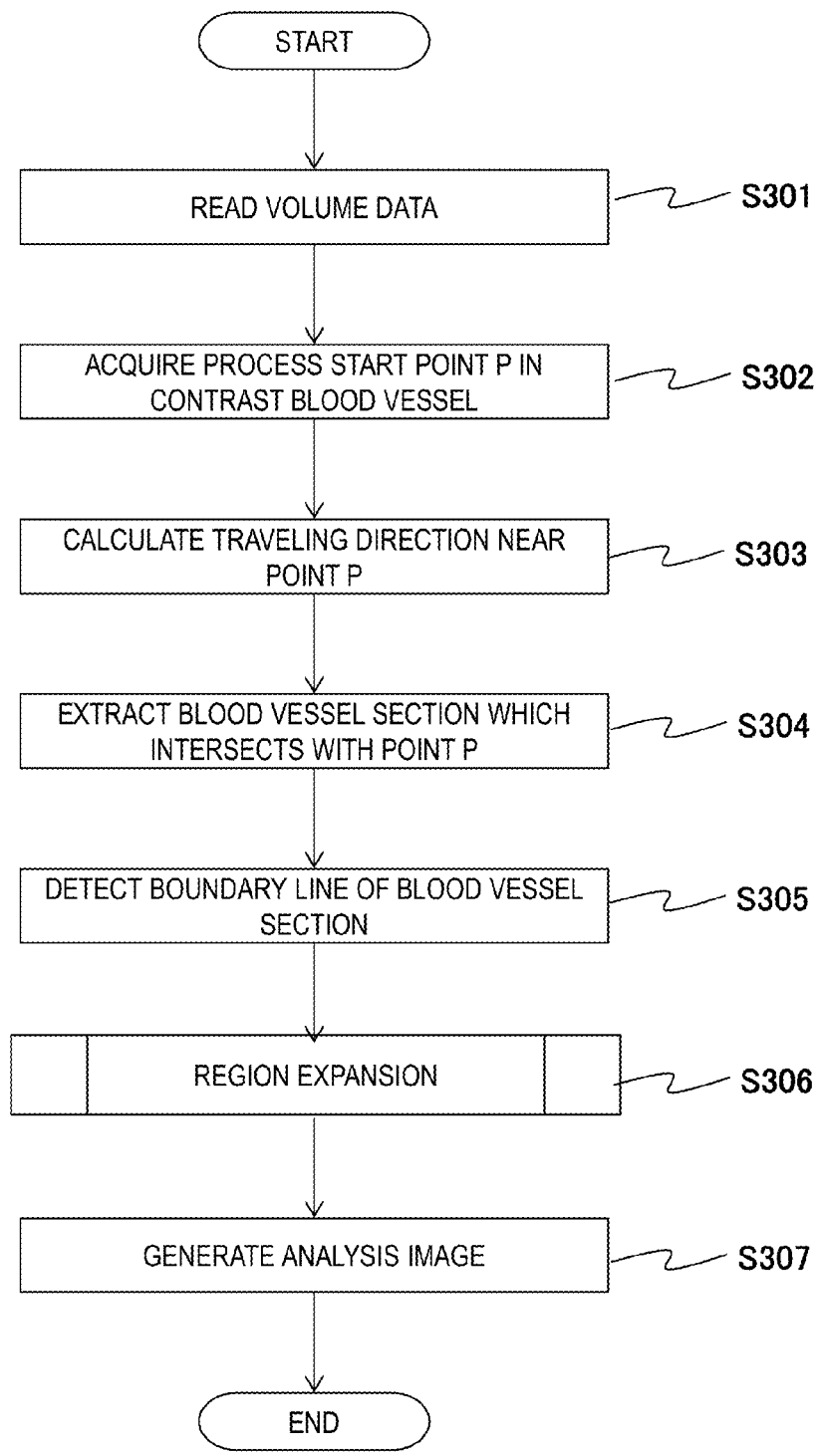
FIG. 12 is a flowchart illustrating the flow of the analysis image generating process performed by the image processing device 100 according to the present invention (third embodiment).

FIG. 12 is a flowchart illustrating a flow of the analysis image generating process according to the third embodiment.

As illustrated in FIG. 12, the CPU 101 reads the volume data which includes the contrast blood vessel (step S301).

Subsequently, the CPU 101 sets an arbitrary point P in the contrast blood vessel to the process starting point. The point P is designated by, for example, a method of the user clicking an arbitrary position of a three-dimensional analysis image, which is generated using the volume data read in step S301, using a mouse. Otherwise, the volume data read in step S301 is analyzed, an upstream part of a thick blood vessel, such as the aorta, where the contrast is not sufficient, is detected, and an arbitrary point included in the detected part may be set to a process starting point P.

Figure 13:
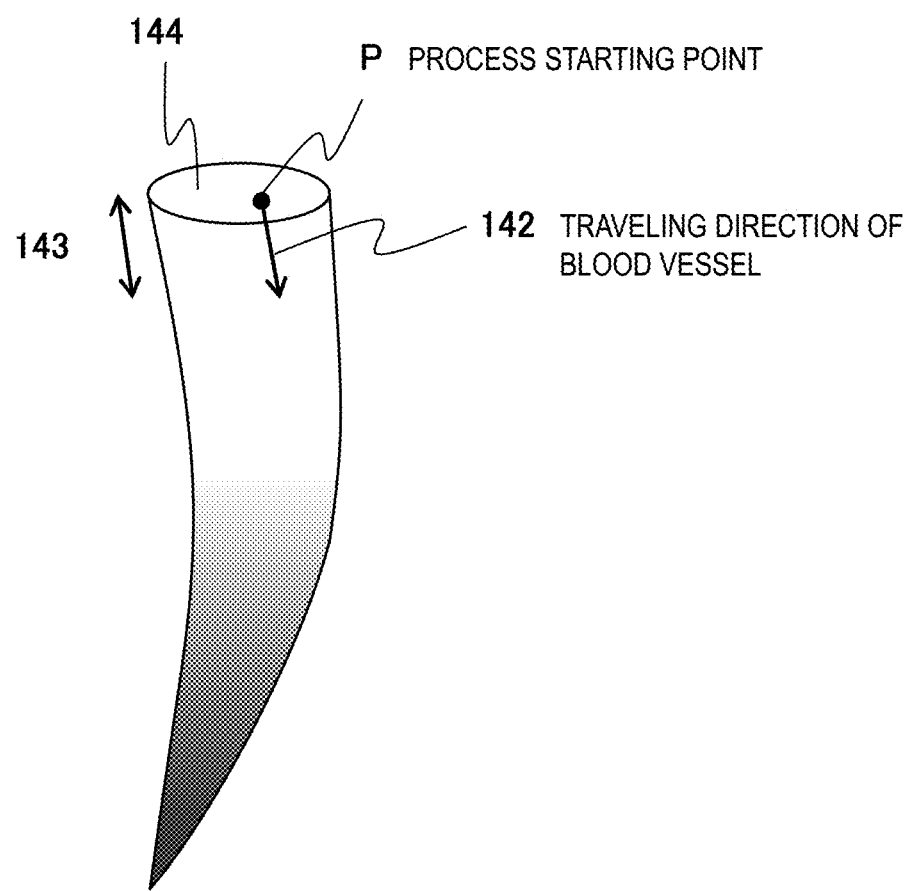
FIG. 13 is a diagram illustrating setting of a process starting point P.

The CPU 101 calculates the traveling direction of the blood vessel near the process starting point P (step S303). As illustrated in FIG. 13, the CPU 101 extracts, for example, a contrast blood vessel 143 near the process starting point P which is designated in step S302 through the region expansion, and performs a thinning process on the extracted contrast blood vessel 143, thereby calculating a traveling direction 142 of the blood vessel. In addition, rays may be scattered in a plurality of directions from the process starting point P, and a direction in which a distance up to the blood vessel surface is the farthest may be set as the traveling direction 142.

In step S303, the CPU 101 extracts a peripheral region of a blood vessel wall toward the calculated traveling direction 142. In a case where the process starting point P is in the middle of the blood vessel, two traveling directions may be preserved in the main memory 102. Otherwise, a direction in which a blood vessel in advance of the point P is long may be set to the traveling direction 142. In a case where the two traveling directions are preserved, respective processes (the extraction of the blood vessel section, the extraction of the boundary line of the blood vessel section, and the region expansion) in steps S304 to S306 are performed for the respective directions.

In a case where the traveling direction of the blood vessel is calculated, the CPU 101 subsequently extracts the blood vessel section which intersects with the point P (step S304). That is, a surface which passes through the process starting point P and is perpendicular to the blood vessel traveling direction, which is calculated in step S303, is acquired as the blood vessel section.

Subsequently, the CPU 101 acquires information of each of the pixels on a boundary line 152 (blood vessel wall) of the blood vessel section (surface 151 of FIG. 14) calculated in step S304 (step S305). That is, the CPU 101 extracts a plurality of pixels on the boundary line 152 of the blood vessel section. The information of each of the extracted pixels on the boundary line 152 is used in a case where the starting point of the region expansion process in step S306 is set.

Subsequently, the CPU 101 performs the region expansion process on a blood vessel surface using some of the pixels on the boundary line 152 detected in step S305 as the starting points (step S306).

The region expansion process on the blood vessel surface performed in step S306 will be described with reference to FIG. 15.

The CPU 101 first determines whether or not the number of starting points, which are set on the boundary line 152 acquired in step S305, is larger than a prescribed threshold (threshold is equal to or larger than 1). In a case where the number of starting points is larger than the threshold (step S401; Yes), the processes in steps S402 to S405 are performed on each of the starting points.

First, the CPU 101 sets the expansion condition of the region expansion process (step S402). In step S402, the CPU 101 uses the gradient information as the expansion condition. The gradient information is a pixel value gradient in a direction over the boundary lines. For example, similarly to the first embodiment, the CPU 101 sets an expandable range R according to a size of the gradient in the pixel of the starting point of the region expansion, and sets a condition such that the pixel included in a prescribed pixel value range in the expandable range R is included in the expansion region.

Figure 14:
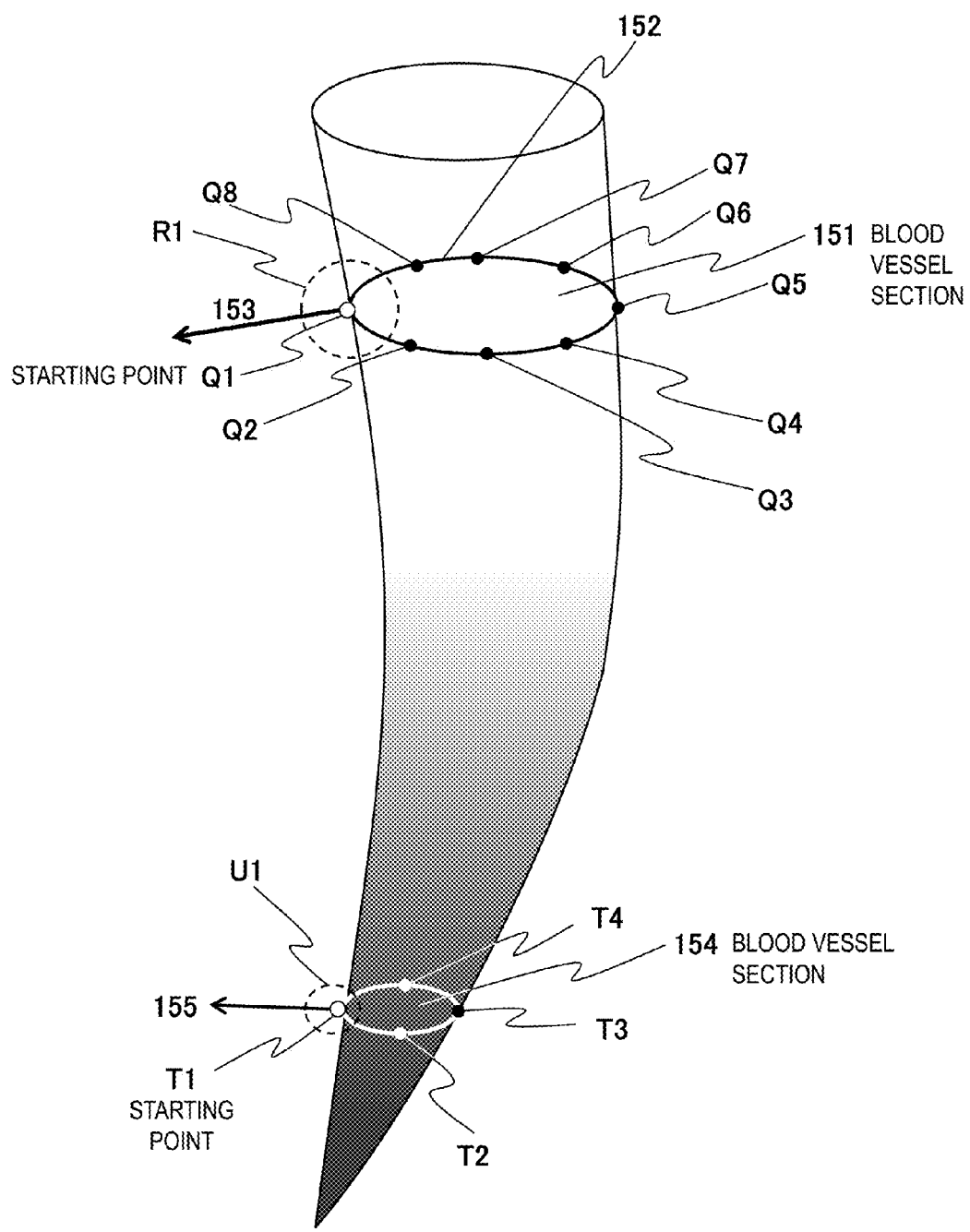
FIG. 14 is a diagram illustrating setting of the expansion condition.

FIG. 14 illustrates an expandable range R1 which is set at a point (starting point Q1) on the blood vessel wall of the blood vessel section 151 near a root of the blood vessel, and an expandable range U1 which is set at a point (starting point T1) on the blood vessel wall of the blood vessel section 154 at an end part.

As illustrated in FIG. 14, in a part (blood vessel section 151) in which the blood vessel is thick and sufficiently contrast-enhanced, the gradient 153 is large in the starting points Q1 to Q8 (pixels on the blood vessel wall in the blood vessel section 151 and on the boundary line 152 between the inside and the outside of the blood vessel) of the region expansion process. In contrast, the blood vessel is thin and is not sufficiently contrast-enhanced at the blood vessel end part, and thus a gradient 155 at starting points T1 to T4 of the region expansion process becomes small. Here, the CPU 101 sets the expandable range to be wide in a case where the gradient is large, and the CPU 101 sets the expandable range to be narrow in a case where the gradient is small (ranges R1 and U1 expressed by broken lines in FIG. 14).

The CPU 101 determines whether or not it is possible to expand a region from the first starting point Q1 for the certain section 151, that is, whether or not the expandable range is "0" according to the expansion condition which is set in step S402 (step S403). In a case where the expandable range is not "0" (step S403; Yes), the process proceeds to step S404. In a case where the expandable range is "0" (step S403; No), the process proceeds to a process which will be performed on the subsequent starting point Q2 in the same section.

In step S404, the CPU 101 performs the region expansion in the expandable range which is set in step S402 (step S404). Here, a condition for the region expansion may be added to the expandable range conditions. It is possible to use, for example, a pixel value, a gradient of the pixel value, an inner product of a gradient of a parent pixel and a gradient of a pixel of interest, second-order differentiation of the pixel value, an inner product of a second-order differentiation of the parent pixel and a second-order differentiation of the pixel of interest, a size of the second-order differentiation in the gradient direction, and the like as parameters which are used in the condition for the region expansion.

In a case where the region expansion process in step S404 is performed, the CPU 101 subsequently moves the starting point of the region expansion to a point on a side of traveling direction of the blood vessel along the surface of the blood vessel (step S405).

Figure 16:
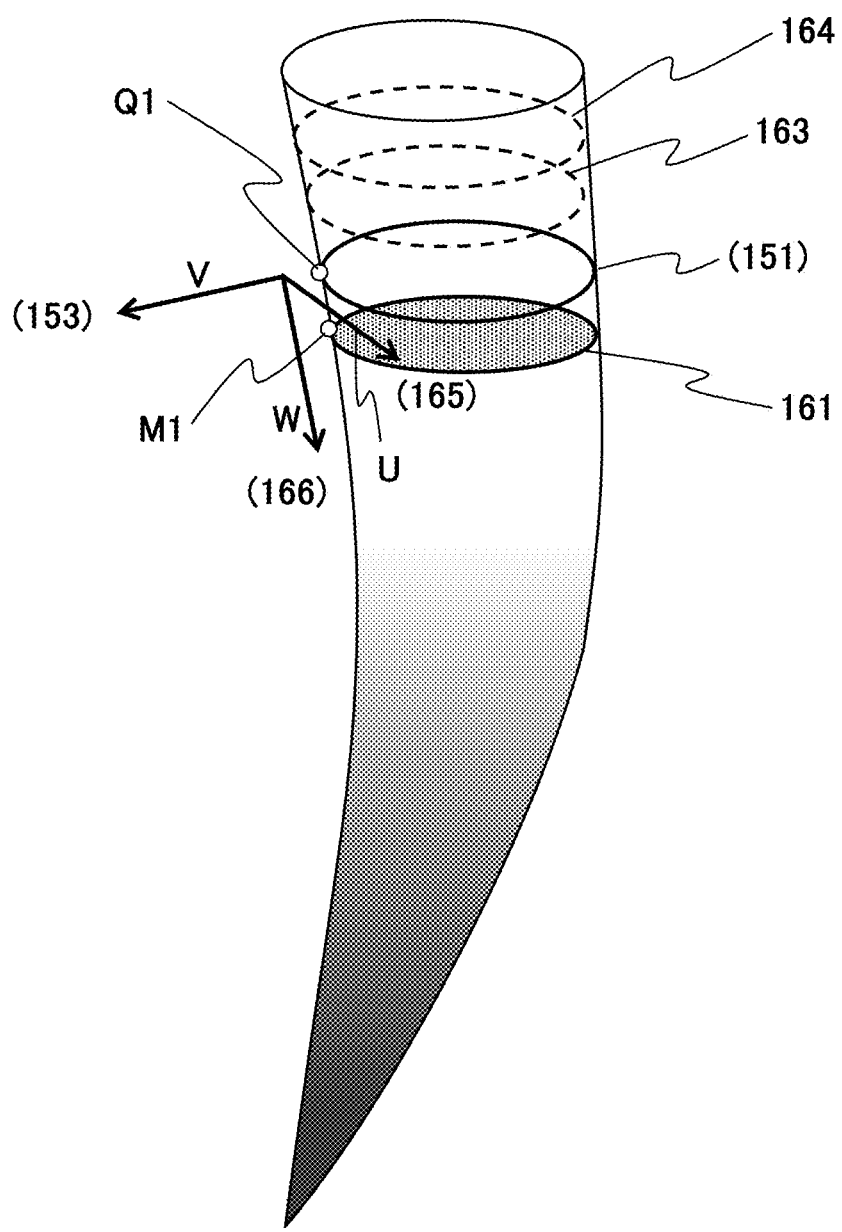
FIG. 16 is a diagram illustrating movement of the starting point in the region expansion (traveling direction of a blood vessel).

Movement of the starting point of the region expansion in the traveling direction of the blood vessel will be described with reference to FIG. 16. The CPU 101 acquires a movement direction 166 (vector W) using an outer product W=U×V of a gradient direction 153 (vector V) of the starting point calculated in step S402 and a tangent direction 165 (vector U) of a sectional region in the starting point Q1.

The CPU 101 moves the starting point of the region expansion toward the movement direction 166 by a predetermined amount, and sets the moved starting point of the region expansion to a subsequent starting point M1.

The CPU 101 repeatedly performs the processes in steps S402 to S405 for each of the starting points Q1 to Q8 in the same blood vessel section. In a case where the region expansion and the movement of the starting point in the traveling direction of the blood vessel end for all the starting points Q1 to Q8 of one blood vessel section, a loop is escaped and the process proceeds to step S406.

At this stage, the expansion region which is expanded from each of the starting points Q1 to Q8 is determined in the blood vessel section 151, and a subsequent starting point M1 (to M8; not illustrated in the drawing) is set on the subsequent blood vessel section 161.

In step S406, the CPU 101 performs a process of thinning or adding the subsequent starting point M1 (to M8) acquired in step S405. In the process of thinning or adding the starting point, the CPU 101 calculates a distance between adjacent starting points in one section, and, in a case where the calculated distance between the starting points is equal to or smaller than a threshold a, the CPU 101 eliminates a one-side starting point (thinning process). In a case where the distance between the starting points is equal to or larger than a threshold b, some starting points are added between the two starting points (adding process). In a case where the distance between the starting points is larger than the threshold a and is smaller than the threshold b, the number of starting points is maintained (step S406).

Figure 15:
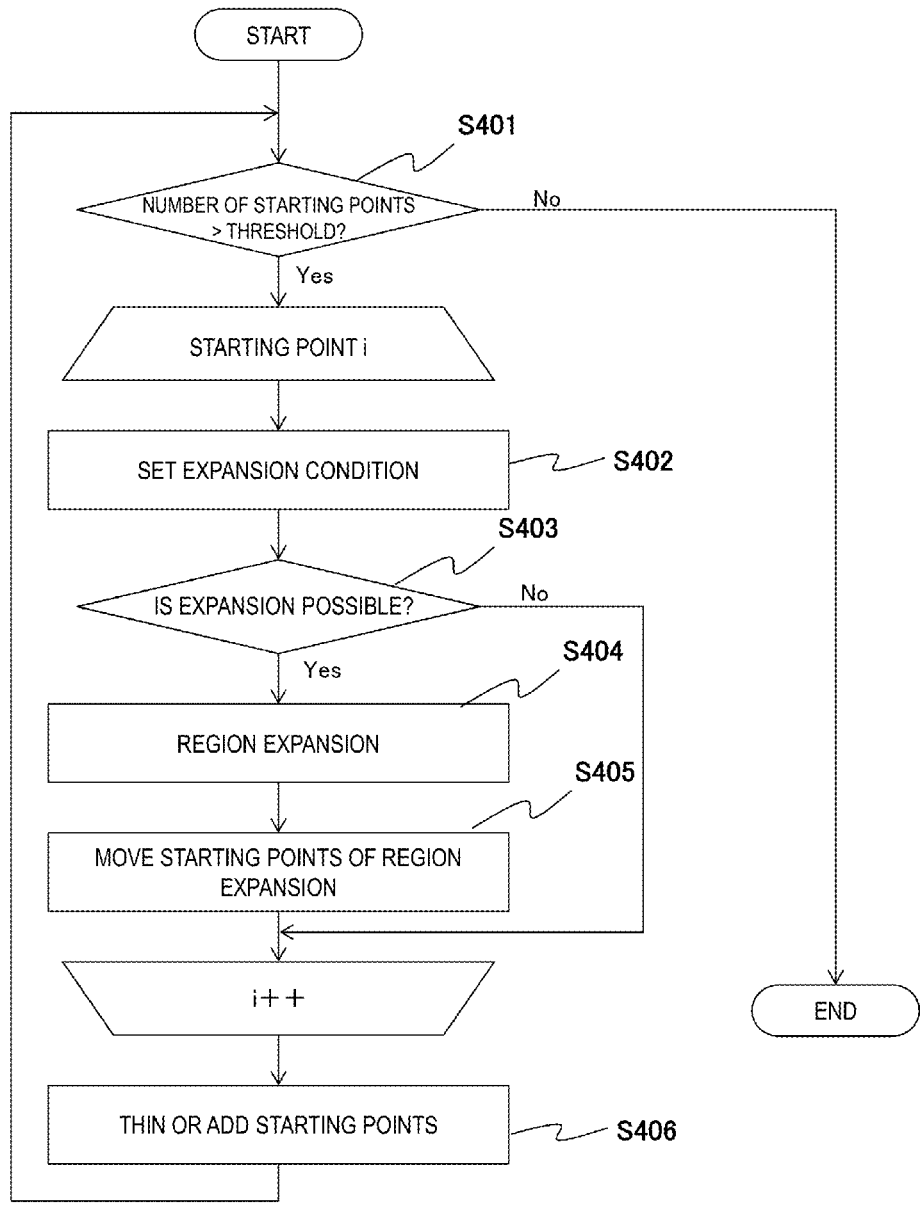
FIG. 15 is a flowchart illustrating a procedure of the region expansion process performed on a blood vessel surface (step S306 of FIG. 12).

As a result of the process illustrated in the flowchart of FIG. 15, a region 173 which is surrounded by a surface 171 and a surface 172 is extracted as illustrated in FIG. 17(b). A thickness of the region 173 is extracted to be thick at the thick part of the blood vessel and the thickness of the region 173 is extracted to be thin at the end part. The CPU 101 performs a process of filling the inside of the surface 172 of the extracted region. In addition, the CPU 101 may perform a process of shrinking a conditional region using a gradient condition or the like, and may eliminate a spare.

Returning to description with reference to FIG. 12, the CPU 101 generates the analysis image using the surface region (region 173 of FIG. 17(b)) of the blood vessel, which is acquired in the region expansion process in step S306, or information of the blood vessel region. In a case where the analysis image is generated, the CPU 101 generates the analysis image by setting the expanded region as a drawing region having a prescribed opacity.

The analysis image may be a virtual endoscopy image in which the inside of the blood vessel is drawn or may be a volume rendering image in which the blood vessel is viewed from the outside. In addition, the central line of the blood vessel may be calculated again based on the region which is extracted in the region expansion process in step S306, and a curved MPR image may be generated based on the central line.

As described above, in the third embodiment, the region expansion is performed using the gradient information of the pixel value from the starting point, which is set on the blood vessel wall of each blood vessel section, as the expansion condition, similarly to the first embodiment. Thereafter, the starting point is moved in the traveling direction of the blood vessel, and the region expansion process is performed from a starting point after the movement at a subsequent section position. The process is repeatedly performed until the end of the blood vessel. Furthermore, in a case where the analysis image is generated, the CPU 101 generates the analysis image by setting the expanded region to the drawing region having the prescribed opacity.

Therefore, it is possible to draw the end part of a contrast blood vessel that includes a part where the contrast is not sufficient.

Hereinabove, although the preferable embodiments of the image processing device according to the present invention are described with reference to the accompanying drawings, the present invention is not limited to the example. It is apparent that those skilled in the art may have easily arrived at various changed examples and modified examples in the categories of the technical spirit disclosed in the specification, and it is understood that those changed examples and modified examples are included in the technical range of the present invention as a matter of course.

REFERENCE SIGNS LIST 1 image processing system
100 image processing device
101 CPU
102 main memory
103 storage device
104 communication I/F
105 display memory
106 I/F
107 display device
108 mouse
109 input device
110 network
111 image database
112 image scanning device
31, 51 air
32 liquid residue (residue)
52 solid residue
33, 53 boundary region between residue and air
34, 54 soft tissue
36, 56 large intestine wall
41 boundary line between the residue and air
45, 46 expandable range
47 expansion region (boundary region)

The invention claimed is:

1. An image processing device including a processor and a non-transitory storage medium storing a program of executable instructions that, when executed by the processor, configure the image processing device to perform a method comprising:
(a) acquiring volume data of an image having a region which exists at a boundary between different substances and has pixel values that are non-uniform and continuously changes;
(b) setting a plurality of starting points for region expansion in the region, and setting an expandable range according to a gradient of the pixel values for each of the starting points as a region expansion condition;
(c) performing a region expansion process in the expandable range from the starting point; and
(d) generating an analysis image from the volume data based on information of an expansion region which is a region expanded through the region expansion process.

2. The image processing device according to claim 1, wherein the region is a boundary region between a contrast residue and air in a luminal organ.

3. The image processing device according to claim 2, wherein the analysis image is generated in (d) by setting a region which is expanded in (c) as a drawing prohibition region.

4. The image processing device according to claim 1, wherein the region is a boundary region between an inside and an outside of a contrast blood vessel which includes a part where the contrast is not sufficient.

5. The image processing device according to claim 3, wherein the analysis image is generated in (d) by setting a region which is expanded in (c) as a drawing region which has a prescribed opacity.

6. The image processing device according to claim 1, wherein the method performed by the image processing device further comprises:
    extracting a first region and a second region from the volume data based on the pixel values and pixel positions of the volume data, and determines the starting point of the region expansion process based on information of the gradient of the pixel values at a boundary between the first region and the second region.

7. The image processing device according to claim 1, wherein the method performed by the image processing device further comprises:
    setting a range of a width according to a size of the gradient of the pixel values for each of the starting points as the region expansion condition to an expandable range.

8. The image processing device according to claim 1, wherein the method performed by the image processing device further comprises:
    extracting a first region and a second region from the volume data based on the pixel values and pixel positions of the volume data;
    setting a scanning line over the first region and the second region; and
    expanding a region up to a prescribed finite range using information of a first order differentiation value of the pixel values on the scanning line, and, thereafter, further expanding the region up to a prescribed finite range using information of a second order differentiation value of the pixel values on the scanning line.

9. The image processing device according to claim 1, wherein, after a region is expanded from the starting point in (c), the starting point is further moved to another section, and the region expansion process is repeated from a position of the starting point after the movement.

10. An image processing method performed by a computer configured into an image processing device by execution of a program of executable instructions in a non-transitory medium, the image processing method comprising:
    acquiring volume data of an image having a region which exists at a boundary between different substances and has pixel values that are non-uniform and continuously changes;
    setting a plurality of starting points for region expansion in the region, and setting an expandable range according to a gradient of the pixel values for each of the starting points as a region expansion condition;
    performing a region expansion process in the expandable range from the starting point; and
    generating an analysis image from the volume data based on information of an expansion region which is a region expanded through the region expansion process.

* * * * *